(12) United States Patent
Kim

(10) Patent No.: US 7,097,602 B1
(45) Date of Patent: Aug. 29, 2006

(54) ABDOMINAL EXERCISER

(76) Inventor: Young-dae Kim, 105, Howan Apt., 44-15, Kwangan3-dong, Suyoung-gu, Busan (KR)

( * ) Notice: Subject to any disclaimer, the term of this patent is extended or adjusted under 35 U.S.C. 154(b) by 610 days.

(21) Appl. No.: 10/069,677

(22) PCT Filed: Aug. 17, 2000

(86) PCT No.: PCT/KR00/00915

§ 371 (c)(1),
(2), (4) Date: Jan. 2, 2003

(87) PCT Pub. No.: WO01/13861

PCT Pub. Date: Mar. 1, 2001

(30) Foreign Application Priority Data

Aug. 21, 1999 (KR) .................... 1999-34801

(51) Int. Cl.
*A63B 26/00* (2006.01)
*A63B 71/00* (2006.01)
(52) U.S. Cl. ............... 482/140; 482/148; D21/680; D21/687
(58) Field of Classification Search ........... 482/140, 482/907, 91, 104–108, 148; D21/680, 687; 219/528; 99/372; 601/84; D24/215
See application file for complete search history.

(56) References Cited

U.S. PATENT DOCUMENTS

| 1,250,392 A | | 12/1917 | Vance |
| 1,697,957 A | * | 1/1929 | Kelly ................. 601/134 |
| 3,943,912 A | | 3/1976 | Nakayama |
| 4,210,134 A | | 7/1980 | Okazaki et al. |
| 4,775,148 A | * | 10/1988 | McLaughlin ............ 482/124 |
| 5,692,996 A | * | 12/1997 | Widerman ............ 482/93 |
| 5,709,634 A | * | 1/1998 | Pointer ................ 482/105 |
| 5,724,687 A | | 3/1998 | Kim |

FOREIGN PATENT DOCUMENTS

| DE | 92 17 987.9 | | 11/1993 |
| JP | 07 236680 | | 9/1995 |
| JP | 7 236680 A | * | 9/1995 |

OTHER PUBLICATIONS

Supplementary European Search Report issued by the European Patent Office in corresponding application EP 00 95 5113 on Apr. 8, 2004.

* cited by examiner

*Primary Examiner*—Lori Amerson
(74) *Attorney, Agent, or Firm*—Buchanan Ingersoll & Rooney PC

(57) ABSTRACT

An abdominal exerciser that can be conveniently applied on the abdomen of a user who is laying down flat is provided. By pushing the abdominal exerciser up and down using the abdominal muscles, abdominal muscles become tones and excess fat can be reduced. The abdominal exerciser includes a flexible plate having a plurality of projections on the bottom surface, for pushing the abdomen down by gravity, and a weigh applying means fixed to the top surface of the flexible plate, for applying its weight to the abdomen.

11 Claims, 6 Drawing Sheets

ABDOMINAL EXERCISER

BACKGROUND OF THE INVENTION

1. Field of the Invention

The present invention relates to an abdominal exerciser, and more particularly, to an abdominal exerciser that can be conveniently applied on the abdomen of a user who is laying down flat. By pushing the abdominal exerciser up and down using the abdominal muscles, abdominal muscles become tones and excess fat can be reduced.

2. Description of the Related Art

Many people these days suffer from various geriatric diseases due to irregular dietary habits, work strains, and lack of exercise. Almost all geriatric diseases are caused by from obesity, and thus a variety of exercises and exercising devices have been suggested so as to eliminate the problems of obesity.

As well known, excess fat first accumulates on the abdomen. Most exercises applied to remove the subcutaneous fat begins with the exercising of other neighboring muscles, other than the abdomen muscles themselves. Thus, such indirect exercise techniques require a user to maintain a steady effort and endure for satisfactory results. Another drawback of the indirect technique lies in that it is not easy for a person with abdominal obesity to continue with such exercise for a long period of time, compared to an average weight person. This is because a person with an obesity problem has a difficult time doing such exercises. Therefore, there is a need for an exerciser that focuses the exercise activity on the abdominal muscles and can be applied conveniently by a user.

SUMMARY OF THE INVENTION

To solve the above problems, it is an objective of the present invention to provide an abdominal exerciser that can be conveniently applied to the abdomen while a user is laying flat, whereby by pushing the abdominal exerciser up and down with a predetermined force using the abdominal muscles, intestinal fat as well as the subcutaneous fat around the abdominal muscles "burns" within a shorter period of time. In addition, the abdominal exerciser can facilitate the vermicular movement of the intestines, thereby relieving constipation.

The objective of the present invention is achieved by an abdominal exerciser comprising: a flexible plate having a plurality of projections on the bottom surface, for pushing the abdomen down by gravity; and a weigh applying means fixed to the top surface of the flexible plate, for applying its weight to the abdomen.

Preferably, the bottom surface of the flexible plate, which has the plurality of projections, is convex.

Preferably, at least one male screw is fixed to the top surface of the flexible plate, and the weight applying means is at least one weights to be engaged with the male screw.

Preferably, the weight applying means comprises a filling for providing weight, and a weight retainer fixed to the top surface of the flexible plate, for holding the filling therein, and the filling comprises metal or mineral.

Preferably, the projections are formed of a mineral capable of emitting far infrared rays, and the abdominal exerciser further comprises a thermal keeping plate below the flexible plate, for keeping the temperature of the abdomen, the thermal keeping plate including a plurality of permanent magnets arranged therein.

Preferably, the abdominal exerciser further comprises a heat emitting plate between the flexible plate and the thermal keeping plate, for producing heat with application of electricity.

Preferably, the abdominal exerciser further comprises a pair of grips at both ends of the flexible plate.

BRIEF DESCRIPTION OF THE DRAWINGS

The above objective and advantages of the present invention will become more apparent by describing in detail preferred embodiments thereof with reference to the attached drawings in which.

DETAILED DESCRIPTION OF THE INVENTION

Figure 1:
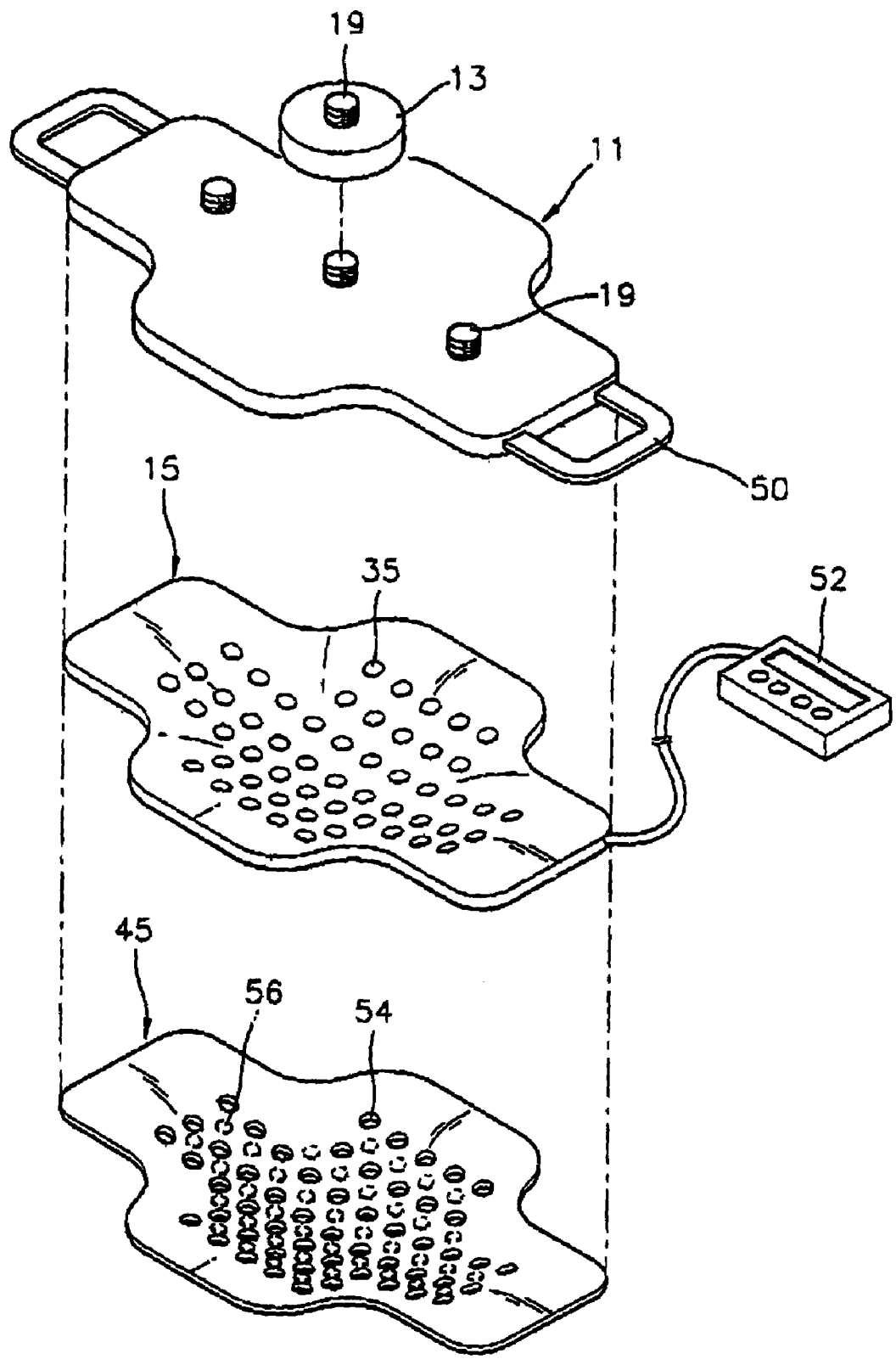
FIG. 1 is a perspective view illustrating the configuration of a first embodiment of an abdominal exerciser according to the present invention.

As shown in FIG. 1, a first embodiment of an abdominal exerciser according to the present invention includes a flexible plate 11 for pushing the abdomen down by gravity when it rests on the abdomen of a user who is laying flat, a plurality of weights 13 installed on the top surface of the flexible plate 11, a heat emitting plate 15 placed below the flexible plate 11, and a thermal keeping plate 45. Here, the bottom surface of the flexible plate 11 refers to the surface facing the abdomen.

Figure 2:
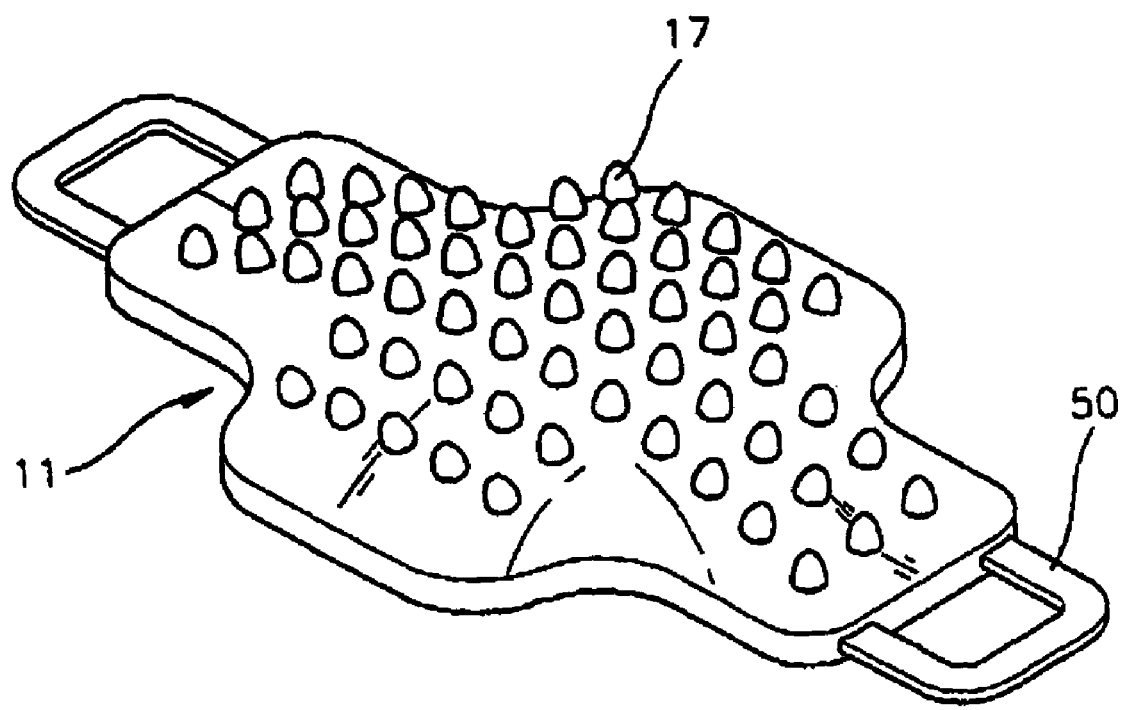
FIG. 2 is a perspective view showing in greater detail the bottom surface of a flexible plate of the abdominal exerciser shown in FIG. 1.

The flexible plate 11 has a planar cross shape, and thus the width of the flexible plate 11 is wider at the center than at both ends. The top surface of the flexible plate 11 is planar, while the bottom surface of the flexible plate 11 is convex, as shown in FIG. 2. The planar surface of the flexible plate 11 is helpful in retaining the weight 13 thereon, and the convex bottom surface of the flexible plate 11 allows the abdomen to be flexed deeply.

Preferably, the flexible plate 11 is formed of plastic, acryl resin or carbon cloth, and the thickness of the flexible plate 11 at the edge is in the range of 5 to 20 mm. Although the material used for the flexible plate 11 has intrinsic elasticity, the flexible plate 11 made from the material also has a rigid property with a predetermined thickness. Thus, the flexible plate 11 is not locally bent but slightly curved by an external force.

Although the flexible plate 11 is formed in a cross shape in the present embodiment, the shape of the flexible plate 11 vary. For example the shape may be in the form of a rectangle, ellipse or polygon.

The flexible plate 11 has a pair of grips 50 at both ends. The grips 50 allow the user to easily move the flexible plate 11 in a horizontal direction on the abdomen to position the flexible plate 11 in place, and allows easy carrying of the flexible plate 11.

Three male screws 19 are fixed to the top surface of the flexible plate 11 perpendicularly, and are engaged with female screws (not shown) threaded at the lower part of each weight 13. Although three male screws 19 are provided in the present embodiment, it will be appreciated that the number of the male screws installed on the flexible plate 11 may vary.

Combining all male screws 19 with the corresponding number of weights 13 is not necessary. In other words, the number of weights 13 to be coupled with male screws 19, and which male screw 19 are to be combined with the weight 13 can be determined by the user depending on the physical conditioning of the user.

A male screw 19 is also provided on the top of each weight 13. The male screw 19 is the same as the male screw 19 fixed to the top surface of the flexible plate 11. The male screw 19, which is able to support a weight 13, allows stacking of the weights 13, thereby flexing the abdomen with greater force.

The heat emitting plate 15 and the thermal keeping plate 45 are positioned below the flexible plate 11. The heat emitting plate 15 is a known means for generating heat with the application of electricity. As the abdominal exerciser according to the present invention rests on the abdomen of a user for exercise, the heat emitting plate 15 generates heat to warm the subcutaneous layer and intestine. The temperature of the heat emitting plate 15 is adjusted by a thermocontroller 52. Alternatively, the heating of the heat emitting plate 15 by the thermocontroller 52 can be suspended as needed. Furthermore, the heat emitting plate 15 may be not installed such that the heat emitting plate 11 directly contact the thermal keeping plate 45.

The heat emitting plate 15 has a plurality of apertures 35. The apertures 35 pass projections 17 (see FIG. 2) formed on the bottom surface of the flexible plate 11 to allow contact with the abdominal skin.

The thermal keeping plate 45 is formed of leather or textile, and is placed in contact with bottom surface of the heat emitting plate 15. When the heat emitting plate 15 is not incorporated into the abdominal exerciser, as previously mentioned, the thermal keeping plate 15 is placed in contact with the bottom surface of the flexible plate 11. The thermal keeping plate 45 has a plurality of apertures 54 which pass through the projections 17 of the flexible plate 11.

The thermal keeping plate 45 includes a plurality of permanent magnets 56. The permanent magnets 56, which are of disk type in the present embodiment, are arranged over and in the thermal keeping plate 45. The permanent magnets 56 generate and infiltrate magnetic field into the subcutaneous fat, thereby facilitating blood circulation. In addition, the thermal keeping plate 45 keeps the abdomen pressed by the flexible plate 11 warm, which prevents heat generated from the abdomen from dissipating and allows sweat at the abdomen. Furthermore, the thermal keeping plate 45 protects the abdomen from the chill of the flexible plate 11.

It is preferable that the thermal keeping plate 45 is formed of a material with skin-like physical properties, for example, synthetic or natural leather.

FIG. 2 is a perspective view illustrating the bottom surface of the flexible plate of the abdominal exerciser shown in FIG. 1 in greater detail.

Referring to FIG. 2, the bottom surface of the flexible plate 11 is entirely curved outwards, and a plurality of projections 17 extend from the surface. As the flexible plate 11 is pushed down on the abdomen, the projections 17 attack the subcutaneous fat and blood vessels, thereby activating flow of blood and energy. Here, the tips of the projections 17 are round. The convex bottom surface of the flexible plate 11 aids in pushing the abdomen deep down, as previously mentioned.

Figure 3:
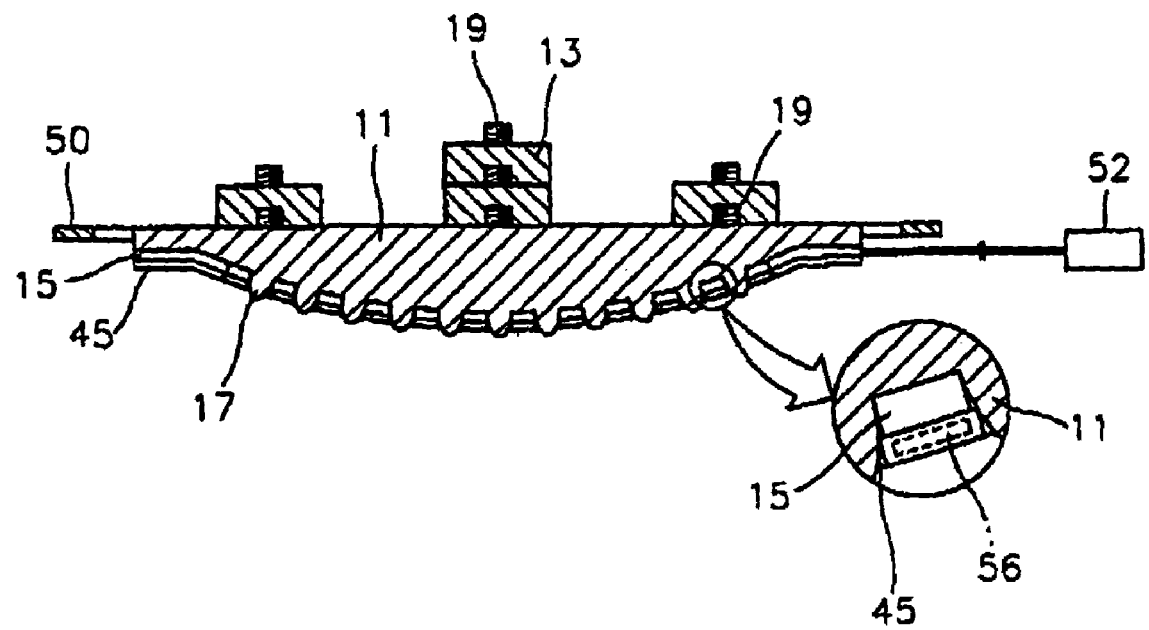
FIG. 3 is a sectional view of an example of the assembly of the abdominal exerciser according to the first embodiment of the present invention.

FIG. 3 is a sectional view of the abdominal exerciser, in which the flexible plate 11, the heat emitting plate 11 and the thermal keeping plate 14 are sequentially stacked is shown.

As shown in FIG. 3, a plurality of weights 13 fixed to the top surface of the flexible plate 11 provide a predetermined weight to the flexible plate 11 to push the abdomen down. In addition, the weights 13 can be layered as shown in FIG. 3, and thus pressure applied to the abdomen can be controlled according to the need of the user.

The heat emitting plate 15 and the thermal keeping plate 45 are attached in sequence close to the bottom surface of the flexible plate 11. A plurality of permanent magnets 56 are present in the thermal keeping plate 45, which provides a magnetic field to the abdomen.

The projections 17 of the flexible plate 11 protrude downward through the apertures 35 and 54 of the heat emitting plate 15 and the thermal keeping plate 45, and directly contact the skin. The projections 17 protrude on the order of 3 to 10 mm relative to the bottom of the heat insulating plate 45.

Figure 4:
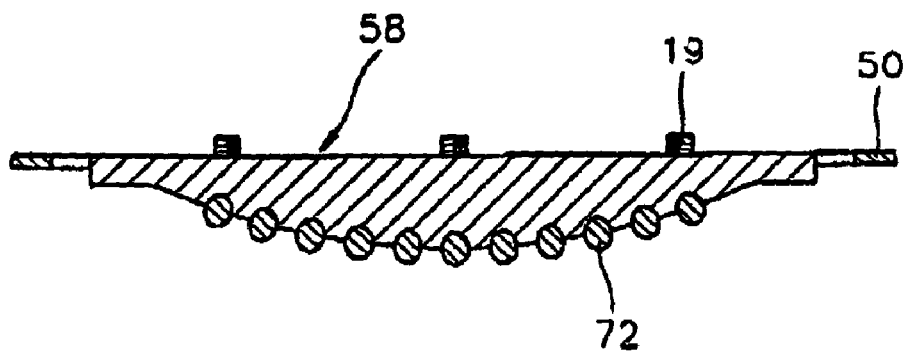
FIG. 4 is a sectional view showing another example of the flexible plate of the abdominal exerciser shown in FIG. 4.

FIG. 4 shows another example of the flexible plate of the abdomen exerciser shown in FIG. 1.

Unlike the projections 17 that extend from the bottom surface of the flexible plate 11 shown in FIG. 3, projection members 72 present in the bottom surface of a flexible plate 58 are formed of a material different from that used for the flexible plate 58, and then attached to the bottom surface of the flexible plate 58. The material used for the projection members 72 may be any of minerals capable of emitting far infrared rays, including germanium (Ge) and jade.

As well known, far infrared rays are effective in reinvigorating a tired human body and relieving his or her chronic fatigue. Thus, as the abdomen is irradiated with far infrared rays, far infrared rays infiltrate into the subcutaneous fat, thereby increasing the exercising effect of the abdominal muscles.

The flexible plate 58 is formed of the same material used for the flexible plate 11 of FIG. 3. Although not shown in FIG. 4, it will be appreciated that a plurality of weights are mounted on the top surface of the flexible plate 58, and a heat emitting plate and a thermal keeping plate are coupled with the flexible plate 58 through the projection members 72 formed at the bottom surface.

Figure 5:
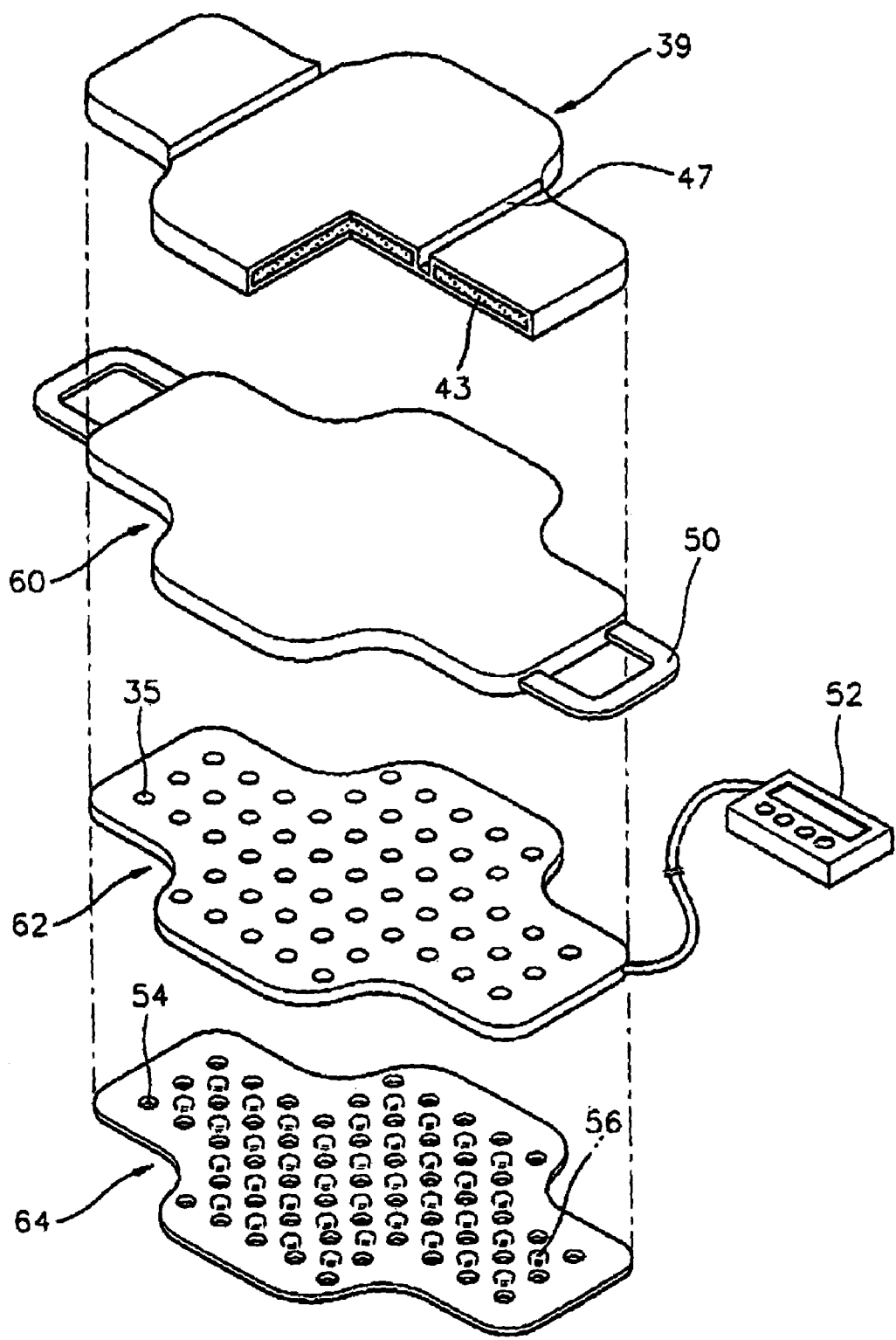
FIG. 5 is an exploded perspective view illustrating the configuration of a second embodiment of an abdominal exerciser according to the present invention.

FIG. 5 is an exploded perspective view of a second embodiment of an abdominal exerciser according to the present invention. In FIG. 5, like reference numerals are used to refer to like elements of FIG. 1.

Referring to FIG. 5, the abdominal exerciser includes a planar flexible plate 60, a weight retainer 39 to be seated on the top of the flexible plate 60, a filling 43 that fills the weight retainer 39 to give weight, and a heat emitting plate 62 and a thermal keeping plate 64, which are placed close to the bottom surface of the flexible plate 60.

Similar to the first embodiment described with reference to FIG. 1, the flexible plate 60 has a width wider at the center than at both ends, which allows complete covering of the abdomen of the user. However, the bottom surface of the flexible plate 60 of the present embodiment is flat. Preferably, the thickness of the flexible plate 60 is in the range of 5 to 20 mm. The flexible plate 60 is formed of the same material used for the flexible plate 11 in the first embodiment.

A pair of grips 50 are fixed to both ends of the flexible plate 60. A plurality of projections 17 (see FIG. 6) are formed at the bottom surface of the flexible plate 60. The projections 17 have round tips and attack the subcutaneous fat and blood vessels.

The heat emitting plate 62 fitted to the bottom surface of the flexible plate 60 provides the same function as that of the heat emitting plate 15 of the first embodiment, and has a plurality of apertures 35 for passing through the projections 17 of the flexible plate 60. A thermal keeping plate 64 placed in contact with the heat emitting plate 62 also has a plurality of apertures 54 for passing through the projections 17. Alternatively, the heat emitting plate 62 may be not installed, such that the thermal keeping plate 64 directly contacts the bottom surface of the flexible plate 60.

The weight retainer 38 seated on top of the flexible plate 60 is formed of plastic, acryl resin or carbon cloth, and is divided into three parts with partitions 47. The internal space of each of the three parts is filled with the filling 43 that is heavy enough to give a predetermined weight to the abdomen. The filling 43 serves as the weights 13 described in the first embodiment with reference to FIG. 1.

The internal space of the three parts of the weight retainer 38 are sealed from the outside, and thus the filling 43 is not drawn out of the weight retainer 38. The filling 43 may be a material that is heavy enough to give a predetermined weight to the abdomen, such as metal or mineral. Examples of the mineral include germanium (Ge), jade, loess and sand. Because the internal spaces of the weight retainer 38 are sealed from the outside, the filling 42 can be in the form of a lump or powder.

Although the weight retainer 38 is divided into three parts in the present embodiment, it will be appreciated that the number of the parts within the weight retainer 38 can be varied.

Figure 6:
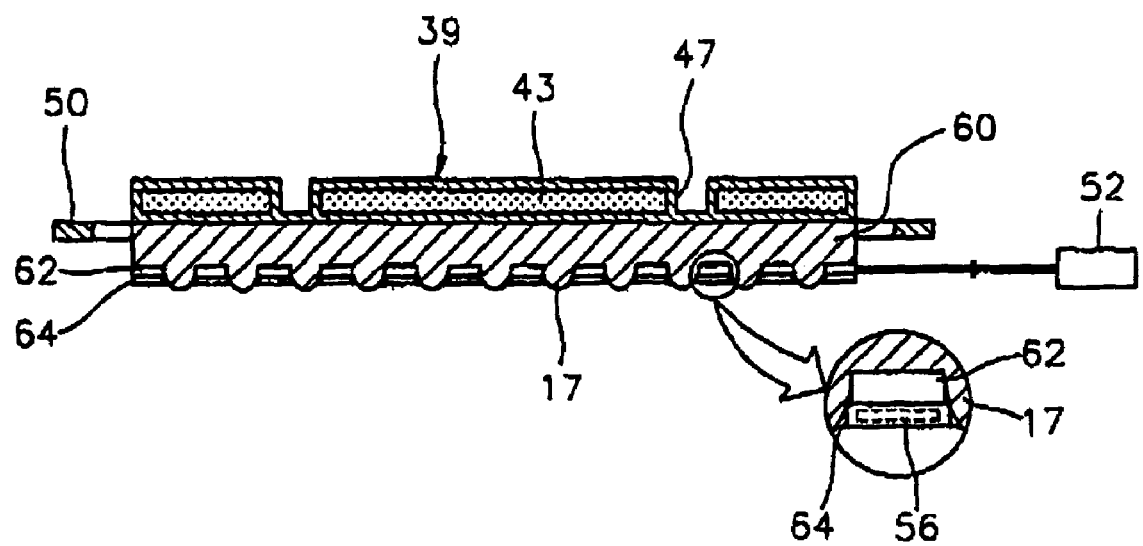
FIG. 6 is a section view of an example of the assembly of the abdominal exerciser according to the second embodiment of the present invention.

FIG. 6 is a sectional view of the abdominal exerciser shown in FIG. 5.

As shown in FIG. 6, the plurality of projections 17 protrude downwards from the bottom surface of the flexible plate 60 through the apertures 35 and 54 of the heat emitting plate 62 and the thermal keeping plate 64. Preferably, the projections 17 protrude on the order of 3 to 10 mm relative to the bottom surface of the thermal keeping plate 64.

A plurality of permanent magnets 56, which produce and infiltrate magnetic field into the subcutaneous fat of the abdomen, are included in the thermal keeping plate 64. In the abdominal exerciser, the permanent magnets 56 and the projections 17 are alternately arranged. The weight retainer 39 on the flexible plate 60 is filled with the filling 43, and pushes the flexible plate 60 down.

Figure 7:
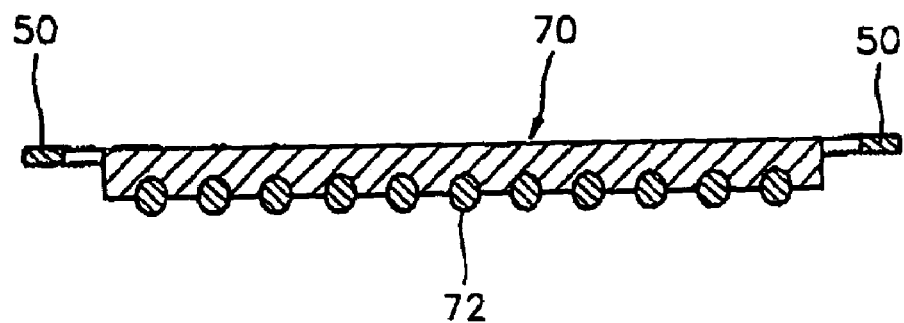
FIG. 7 is a sectional view showing another example of a flexible plate of the abdominal exerciser according to the second embodiment of the present invention.

FIG. 7 shows another example of the flexible plate adopted in the abdominal exerciser of FIG. 5.

Unlike the projections 17 that extend from the bottom surface of the flexible plate 60 shown in FIG. 6, projection members 72 present in the bottom surface of a flexible plate 70 are formed of a material different from that used for the flexible plate 70, and then attached to the bottom surface of the flexible plate 70. The material used for the projection members 72 may be any of known minerals capable of emitting far infrared rays, including germanium (Ge) and jade.

Although not shown in FIG. 7, it will be appreciated that the weight retainer 39 filled with the filling 43 is placed on the flexible plate 70, and a heat emitting plate and a thermal keeping plate are coupled with the flexible plate 70 through the projection members 72 formed at the bottom surface.

When the abdomen exerciser having the above configuration, for example, equipped with the flexible plate 60 or 70, is positioned on the abdomen of a user, the projections 17 or the projection members 72 are made to contact the abdomen by the weight of the filling 43, and magnetic field from the permanent magnets 56, and/or far infrared rays from the projection members 72 infiltrate into the subcutaneous layer, thereby stimulating the blood vessels and activating the flow of blood in the subcutaneous fatty layer.

As the user is laying down flat and breaths from the abdomen with the abdominal exerciser on the abdomen, the abdominal exerciser is moved upward and downward, and in turn the subcutaneous fatty layer is slowly burned with time. At this time, heat generated from the abdomen is kept by the thermal keeping plate fitted to the bottom surface of the flexible plate, which allows the user to sweat while exercising, similar to being in a steam room. Furthermore, the abdomen can be heated for more effective exercise with the heat emitting plate as needed.

Figure 8:
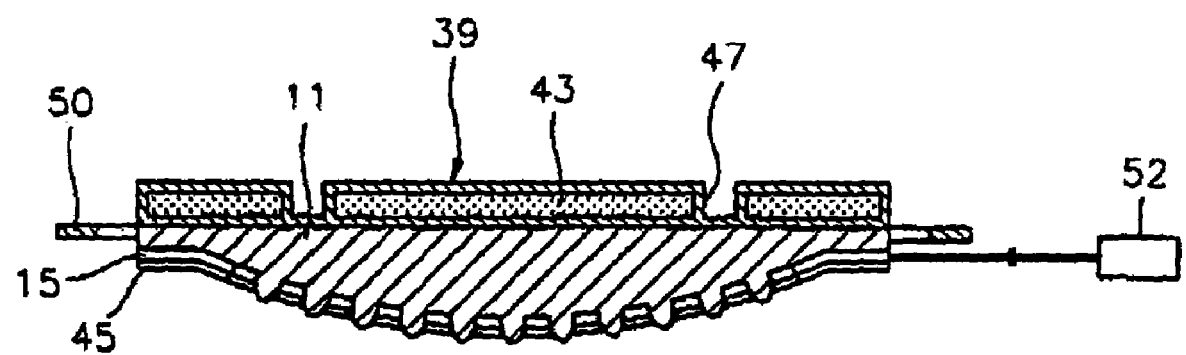
FIG. 8 illustrates a hybrid configuration of the abdominal exercisers according to the first and second embodiments of the present invention.

FIG. 8 illustrates a combination of the flexible plate 11 of the first embodiment with the weight retainer 39 of the second embodiment.

As shown in FIG. 8, the weight retainer 39 filled with the filling 43, instead of the weights 13, is fitted to the top surface of the flexible plate 11 having the convex bottom surface, so as to apply a predetermined weight to the abdomen. Alternatively, the flexible plate 60 having the planar bottom surface of the second embodiment may be combined with the weights 13 of the first embodiment. In other words, any type of weight whose weight is sufficient to apply a predetermined pressure through the flexible plate to the abdomen can be utilized.

The effect of the abdominal exerciser according to the present invention was evidenced by the inventors. The results are shown in Table 1.

TABLE 1

| Gender | Abdominal Obesity Index before Exercising | Exercising Period of Time with Abdominal Exerciser (weeks) | | | | | |
|---|---|---|---|---|---|---|---|
| | | 1 | 2 | 3 | 4 | 5 | 6 |
| Male | 1.2 | 1.1 | 1.05 | 1.05 | 1.0 | 1.0 | 1.0 |
| | 1.5 | 1.4 | 1.35 | 1.3 | 1.25 | 1.2 | 1.1 |
| Female | 1.2 | 1.1 | 1.05 | 1.0 | 0.95 | 0.9 | 0.9 |
| | 1.4 | 1.3 | 1.35 | 1.3 | 1.2 | 1.2 | 1.15 |

In Table 1, the abdominal obesity index refers to a waist-to-hip measure ratio. In the United States, the base line for abdominal obesity evaluation is 0.95 or more for males, and 0.8 or more for females. In Europe, the base line is 0.9 or more for males and 0.8 or more for females.

In Korea, a reliable base line for abdominal obesity evaluation has not been established yet. However, in practice, if the abdominal obesity index is 1.0 or more for males, and 0.9 or more for females, it is determined to be abdominal obesity.

As shown in Table 1, the abdominal obesity index starts to decrease after just 1-week of use of the exerciser. Also, after 4-week of use of the exerciser, the abdominal obesity index drops to almost the same level as a normal condition.

While this invention has been particularly shown and described with reference to preferred embodiments thereof, it will be understood by those skilled in the art that various changes in form and details may be made thereto without departing from the spirit and scope of the invention as defined by the appended claims.

As previously mentioned, the abdominal exerciser according to the present invention can be effectively utilized in burning subcutaneous fatty layer around the abdominal muscles by just letting a user take breaths while laying flat with the abdominal exercisers having a predetermined weight on his or her abdomen. As a result, excess fat around the abdomen can be easily decomposed within a short period of time. In addition, use of a heat emitting plate and permanent magnets activate movement of the intestines and the flow of blood during exercising, which enables to decompose intestinal fat and activate a function of the intestines. As a result, digestion and absorption in the human body facilitates, and constipation can be relieved.

While this invention has been particularly shown and described with reference to preferred embodiments thereof, it will be understood by those skilled in the art that various changes in form and details may be made thereto without departing from the spirit and scope of the invention as defined by the appended claims.

What is claimed is:

1. An abdominal exerciser comprising:
   a flexible plate having a plurality of projections on the bottom surface thereof;
   a weight applying means fixed to the top surface of the flexible plate and adapted to apply a predetermined weight to the flexible plate and thereby to push an abdomen down during exercise; and
   a thermal keeping plate stacked to the bottom surface of the flexible plate and operative to prevent heat generated by the abdomen from dissipating, said thermal keeping plate having a plurality of apertures for passing the projections therethrough,
   wherein said projections contact the skin of the abdomen and attack subcutaneous fat of the abdomen when the exerciser is placed on the abdomen.

2. The abdominal exerciser of claim 1, wherein the bottom surface of the flexible plate is convex.

3. The abdominal exerciser of claim 1, wherein at least one male screw is fixed to the top surface of the flexible plate, and wherein the weight applying means includes at least one weight that engages the male screw.

4. The abdominal exerciser of claim 1, wherein the weight applying means comprises a filling for providing weight and a weight retainer fixed to the top surface of the flexible plate and configured to hold the filling therein, and wherein the filling comprises metal or mineral.

5. The abdominal exerciser of claim 1, wherein the projections are formed of a mineral capable of emitting far infrared rays, and wherein the thermal keeping plate includes a plurality of permanent magnets arranged therein.

6. The abdominal exerciser of claim 5, further comprising a heat emitting plate disposed between the flexible plate and the thermal keeping plate and operative to generate heat upon application of electricity and thereby to warm the subcutaneous fat and an intestine of the abdomen.

7. The abdominal exerciser of claim 1, further comprising a pair of grips affixed to the flexible plate.

8. The abdominal exerciser of claim 2, wherein at least one male screw is fixed to the top surface of the flexible plate, and wherein the weight applying means includes at least one weight that engages the male screw.

9. The abdominal exerciser of claim 2, wherein the weight applying means comprises a filling for providing weight and a weight retainer fixed to the top surface of the flexible plate and configured to hold the filling therein, and wherein the filling comprises metal or mineral.

10. The abdominal exerciser of claim 2, wherein the projections are formed of a mineral capable of emitting far infrared rays, and wherein the thermal keeping plate includes a plurality of permanent magnets arranged therein.

11. The abdominal exerciser of claim 10, further comprising a heat emitting plate disposed between the flexible plate and the thermal keeping plate and operative to generate heat upon application of electricity and thereby to warm the subcutaneous fat and an intestine of the abdomen.

* * * * *